United States Patent [19]
Haehner et al.

[11] 3,977,231
[45] Aug. 31, 1976

[54] STATIC COEFFICIENT TEST METHOD AND APPARATUS

[75] Inventors: Carl L. Haehner, Dayton; John L. Tarpley, Rockville, both of Md.

[73] Assignee: The United States of America as represented by the Administrator of the National Aeronautics and Space Administration, Washington, D.C.

[22] Filed: June 9, 1975

[21] Appl. No.: 585,420

[52] U.S. Cl. .................................................. 73/9
[51] Int. Cl.² ........................................ G01N 19/02
[58] Field of Search ................... 73/9, 10, 7, 89; 35/19 R

[56] References Cited
UNITED STATES PATENTS

| | | | |
|---|---|---|---|
| 1,668,593 | 5/1928 | Jones | 73/9 |
| 2,493,782 | 1/1950 | Schwarz | 73/9 |
| 3,059,464 | 10/1962 | Deane | 73/9 |
| 3,245,253 | 4/1966 | Gruber | 73/9 X |
| 3,721,115 | 3/1973 | Kearns | 73/9 |
| 3,785,196 | 1/1974 | Smith | 73/10 X |

*Primary Examiner*—Richard C. Queisser
*Assistant Examiner*—Daniel M. Yasich
*Attorney, Agent, or Firm*—John O. Tresansky; Robert D. Marchant; John R. Manning

[57] ABSTRACT

The static coefficient of friction between contacting surfaces of a plurality of bodies is determined by applying a load to the bodies in a direction normal to the contacting surfaces. Opposite ends of a flexible filament are fixedly connected to a load cell and a first of the bodies. A motor continuously moves a second of the bodies away from the load cell at constant velocity to pull the first body at right angles to the force of the normal load so that the first body moves intermittently relative to the second body across a contact surface between them. The load on the surfaces, the nature of the surfaces, and the speed of the first body relative to the load cell are such that the filament is alternately and cyclically tensioned and relaxed as the movement occurs. The maximum tension occurs at the incipient stages of movement of the first body relative to the second body. The load cell derives a series of measurements which are coupled to an x–y recorder, from which the maximum forces of the filament are determined to enable the static coefficient of friction to be determined. From the maximum forces and the normal force, the coefficient is determined. For determining coefficients of friction where there are large compression loads, the normal load is applied with a calibrated compression spring that is deflected by a predetermined amount determined by a spring load vs. deflection calibration curve.

11 Claims, 5 Drawing Figures

STATIC COEFFICIENT TEST METHOD AND APPARATUS

ORIGIN OF THE INVENTION

The invention described herein was made by employees of the U.S. Government and may be manufactured and used by or for the Government for governmental purposes without the payment of any royalties thereon or therefor.

FIELD OF THE INVENTION

The present invention relates generally to a method and apparatus for determining the static coefficient of friction between contacting surfaces of a plurality of bodies, and more particularly to a method and apparatus wherein a flexible filament fixedly connected to one of the bodies is alternately and cyclically tensioned and relaxed in response to another of the bodies being moved at constant velocity relative to a fixed portion of the filament. In accordance with another aspect of the invention, coefficients of friction for contacting surfaces under high compressive loads up to 600 p.s.i. are determined by utilizing a test fixture including a calibrated compression spring that exerts a normal force on the contacting surfaces.

BACKGROUND OF THE INVENTION

As is well known, the coefficient of static friction is a proportionality constant, $f$, relating the maximum amount of force required to translate one body relative to another body to cause incipient relative movement between the bodies (the maximum force of static friction, ($F$), to overcome a force ($N$) normal to the direction of movement and is mathematically given by $f = F/N$.

Prior art methods and apparatus for determining the static coefficient of friction between a plurality of bodies having contacting surfaces have involved connecting a relatively inflexible filament to one of the bodies and applying a constant force to the filament, whereby a constant force is applied to the one body. The bodies are loaded with a normal force of predetermined magnitude, usually by mounting the bodies horizontally and placing a weight on the upper body. The force on the filament at the moment of incipient movement between the contacting surfaces is determined to enable the static coefficient of friction to be calculated. After the incipient movement, movement of one of the bodies relative to the other body at constant speed is continued by pulling the inflexible cable at constant speed. The force on the inflexible cable is determined to enable the kinetic coefficient of friction to be determined. Hence, this standard procedure, which is reported in the 1970 Annual Book of ASTM Standards, pages 544–548, is not suitable for quickly and easily making a series of tests to determine the static coefficient of friction. If it is desired to conduct a series of tests to determine static friction so that increased reliability of the static friction determination can be obtained, it is necessary with the prior art technique and apparatus to set up the apparatus multiple times. Of course, it is undesirable to set up an apparatus a number of times in order to take multiple tests because of the time and expense involved, as well as because of the possibility of unreliable measurements between different setup procedures.

It is, accordingly, an object of the present invention to provide a new and improved method of and apparatus for determining the static coefficient of friction between contacting surfaces of a plurality of bodies.

A further object of the invention is to provide a new and improved method of and apparatus for enabling the coefficient of static friction between contacting surfaces of a plurality of bodies to be determined from a series of measurements which require only a single setup of the testing equipment.

Prior art devices and methods for testing the static coefficient of friction have generally been designed for determining coefficients of friction under light compressive loads. However, there are certain situations wherein the coefficient of the friction must be determined for extremely heavy loads. We have found that the normal load provided by a weight, as indicated by the prior art test apparatus and methods, does not provide the required stress levels.

It is, accordingly, a further object of the invention to provide a new and improved apparatus for and method of testing for the coefficient of static friction in situations wherein the coefficient is considerably in excess of one.

Another object of the invention is to provide a new and improved method of and apparatus for enabling static coefficient of friction tests to be determined at stress levels on the order of 600 p.s.i.

BRIEF DESCRIPTION OF THE INVENTION

In accordance with one aspect of the invention, a series of tests to determine the static coefficient of friction between contacting surfaces of a plurality of bodies is made with a single setup by connecting a flexible filament to one of the bodies and continuously moving this body away from a second body via the filament at a constant velocity while the bodies are loaded in a direction normal to the direction in which the filament pulls on the first body. Thereby, the first body moves intermittently relative to the second body across a contact surface between the two bodies and the filament is alternately and cyclically tensioned and relaxed as the movement occurs. The maximum tension occurs at incipient stages of movement between the two bodies so that the force on the filament when maximum tensioning occurs is indicative of the maximum static friction force.

A load cell is connected to the fixed portion of the filament and provides indications of the force on the filament. The load cell measurements are coupled to an x–y recorder, that is driven in one direction in response to the force measurement and is driven in a second direction as the second body is being moved away from the load cell. Thereby, the x–y recorder provides a chart with an indication of the cyclic forces on the flexible filament. The maximum force during each cycle provides an indication of the force of static friction for each cycle. A series of readings for the maximum value of static friction is obtained without readjusting the measuring equipment or involving a new setup each time a different test for coefficient of friction between the same materials is desired.

In accordance with another aspect of the invention, the static coefficient of friction for regimes wherein the normal loads are considerably greater than usual, i.e., wherein a stress on the order of 600 p.s.i. is applied to the contacting surfaces, is provided by applying the normal force with a calibrated, coil-type spring that compresses the two bodies. The compression spring is deflected by an amount indicated by a calibrated spring deflection versus load compression response characteristic. Another advantage of utilizing a calibrated compression spring as a member for applying a normal load to the contacting surfaces being tested for static coefficient of friction is that the normal load can easily be varied by varying the deflection of the spring. Also, such a spring makes it possible to easily measure the coefficient of static friction of face plates or other members having a relatively small cross-sectional contacting surface to be tested since the force at one end of the spring is applied to the tested surfaces through an end plate.

It is, accordingly, a further object of the invention to provide a new and improved apparatus for and method of determining the static coefficient of friction with a member that is easily adjusted to provide varying normal loads to the contacting surfaces being tested for static coefficient of friction.

The above and still further objects, features and advantages of the present invention will become apparent upon consideration of the following detailed description of several specific embodiments thereof, especially when taken in conjunction with the accompanying drawing.

DETAILED DESCRIPTION OF THE DRAWING

Figure 1:
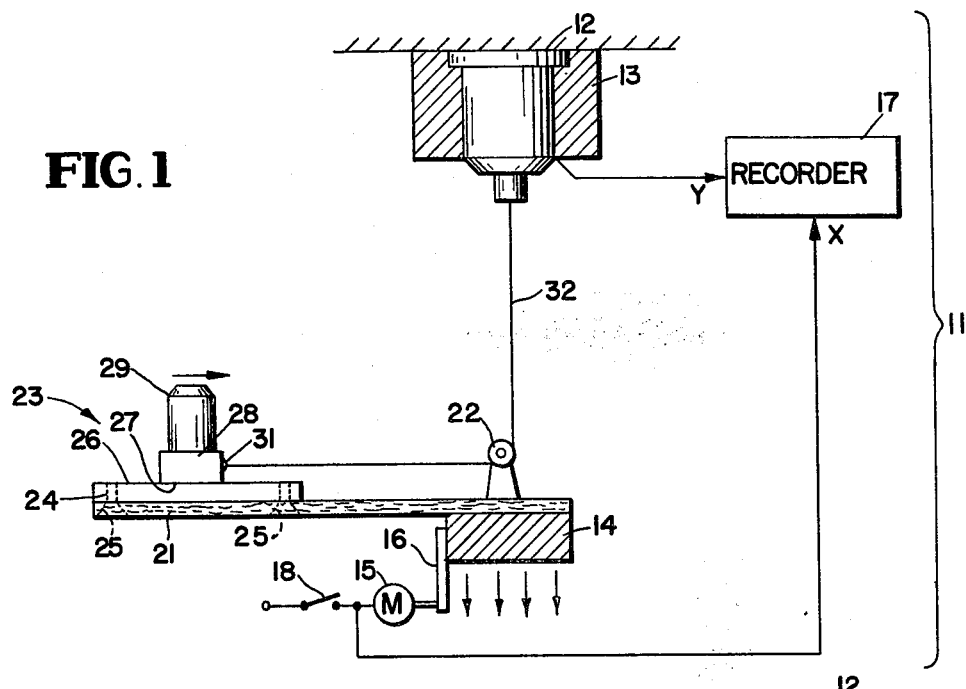
FIG. 1 is a schematic diagram of one embodiment of the apparatus for conducting the method of the present invention.

Reference is now made to FIG. 1 of the drawing wherein there is illustrated, in schematic form, a test apparatus in accordance with one embodiment of the invention wherein a force measuring load cell 12 is fixedly mounted in a stationary cross head 13 of a universal testing instrument 11, such as a Model TTC Instron Universal Testing Instrument. The universal testing machine 11 includes moving cross head 14 that is translated vertically away from stationary cross head 13 at constant speed and velocity by a constant speed motor 15 that drives the cross head through lead screw 16. Also included in the universal testing machine 11 is a conventional $x$–$y$ chart recorder 17, having a $y$-axis input responsive to a force signal derived from load cell 12 and an $x$-axis constant speed input that moves in synchronism with the translation of cross head 14 away from cross head 13. To this end, constant speed motor 15 and a constant speed motor in recorder 17 are connected to a suitable a.c. power supply through switch 18 which is manually activated for the duration of a test.

Fixedly mounted on moving cross head 14 is a horizontally extending arm 21 on which is fixedly mounted a low friction, ball bearing pulley 22, of the type that is frequently referred to as a frictionless pulley. Pulley 22 is positioned immediately below load cell 12 so that a vertical line exists between the center of the load cell and the right, circumferential edge of the pulley, as viewed in FIG. 1. Positioned at the end of arm 21 remote from pulley 22 is a test fixture 23. Test fixture 23 includes plate 24 that is fixedly mounted on arm 21 by bolts 25. The upper surface 26 of plate 24 is prepared by coating or machining, to form a contact surface of one of the bodies being tested for the static coefficient of friction. The other contact surface is formed by the lower planar surface 27 of body 28 that rests on the upper, planar surface 26 of plate 24. Body 28 is loaded with a suitable weight 29 that rests on the upper surface of body 28 and provides a force normal to the contact area between surfaces 26 and 27. On a sidewall of body 28 facing pulley 22, tab 31 is fixedly secured. The center of tab 31 is at the same height above the surface of arm 25 as the bottom, circumferential edge of pulley 22 so that a horizontal line extends between them.

Fixedly connected between load cell 12 and tab 31 are the two end portions of a very flexible, high strength filament 32 that is wound over pulley 22. Thereby, filament 32 extends vertically from load cell 12 to the right edge of pulley 22 and around the pulley to tab 31 in a horizontal direction. In one preferred embodiment, filament 32 is a multistrand, stainless steel wire wherein each of the strands is coated with a suitable low friction coating; exemplary of a suitable, very flexible, high strength filament is a wire formed of 300 strands of 10 micron coated wire commercially known as Brunsmet.

In operation, after the apparatus has been initially set up as illustrated, switch 18 is closed and cross head 14 begins to move vertically away from load cell 12. With sufficient movement of cross head 14 away from load cell 12, filament 32 becomes tensioned sufficiently to exert a horizontal force against body 28 to cause the body to be translated toward the pulley 22. The speed of cross head 14, the coefficient of the static friction between surfaces 26 and 27 and the nature of filament of 32 are such that the filament relaxes immediately after initial movement of body 28 toward pulley 22. In response to filament 32 relaxing, the horizontal force applied by the filament to the body is reduced and further translation of the body 28 and weight 29 toward pulley 22 ceases. With further movement of cross head 14 and plate 24 away from load cell 12, filament 32 again becomes sufficiently tensioned to exert sufficient horizontal force against body 28 to cause translation of the body toward the pulley 22. Filament 32 again relaxes and further translation of body 28 and weight 29 toward pulley 22 ceases. Thereby, there is intermittent and cyclic tensioning and relaxation of filament 32 in response to the movement of fixed plate 24 away from load cell 12, which results in an intermittent and cyclic movement of body 28 and weight 29 toward pulley 22.

Figure 5:
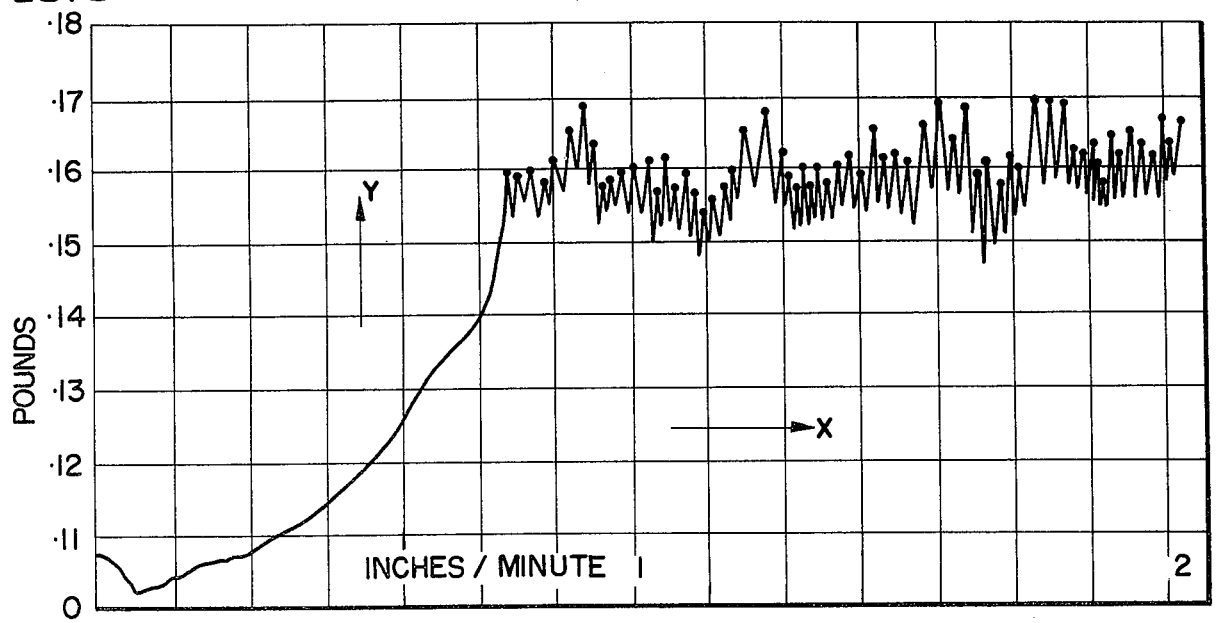
FIG. 5 is a typical plot of data obtained from an $x$–$y$ recorder utilized with the apparatus of FIG. 1.

Load cell 12 measures the cyclically varying forces applied to filament 32 as a result of the cyclic tensioning and relaxing of the filament. A typical response of load cell 12, as indicated by the output of $x$–$y$ recorder 17, is illustrated in FIG. 5 wherein the force pounds on load cell 12 is indicated by the $y$-axis displacement, and the vertical separation between fixed plate 24 and the load cell, which is correlated with time, is indicated by the $x$-axis coordinate in inches/minute. The curve of FIG. 5 was derived for a normal load exerted by weight 29 of 1.03 lbs. against the tested bodies 29, for a constant vertical translation of cross head 14 of 1 inch per minute; for this particular test, contact surface 27 was a 1 inch square of smooth aluminum sliding across a 2 inch square surface 26 of smooth copper.

It is noted that the force measured by load cell 12 and indicated by the chart of FIG. 5 cycles through a large number of maximum values. Each maximum value is indicated by a dot on the graph and occurs at the incipient stages of movement of body 28 across plate 24. In the chart of FIG. 5, 63 peak values appear over a 2 minute time interval required for the 1 square inch plate 28 to move from one end to the other end of the 2 square inch plate 24. The peak values are read from the chart and averaged together to determine the statistical value for the coefficient of friction between the contact surfaces 26 and 27. By way of example, the average force of all 63 peaks recorded on the x–y recorder is substantially 0.162 lbs. The static coefficient of friction is determined by the ratio of this average force to the normal force of 1.03 lbs exerted on contacting surfaces 26 and 27. In the example presented the static coefficient of friction is then given by the ratio of 0.162 lbs/1.03 lbs which approximately equals 0.158. If desired, the variance or standard deviation of the readings can be obtained by utilizing standard statistical formulae.

Figure 2:
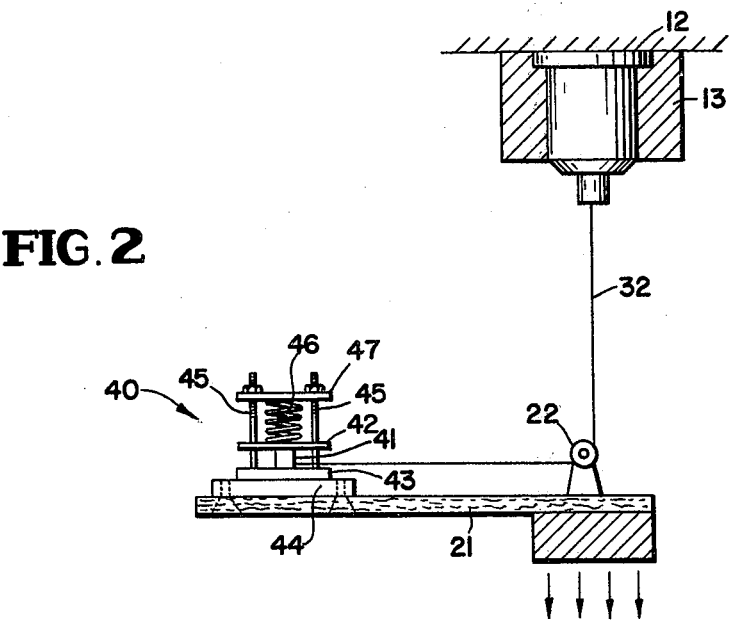
FIG. 2 is a schematic diagram of a second embodiment of the apparatus for conducting the method of the invention.

To determine the coefficient of static friction between contacting surfaces of a plurality of bodies under high stress levels on the order of 600 p.s.i., the apparatus of FIG. 1 is modified as indicated by FIG. 2. In FIG. 2, test fixture arrangement 23 is replaced with a test fixture 40 that is able to exert a high pressure between the adjoining, contacting upper face of test block or specimen 41 and the lower face of plate 42, as well as between the contacting lower face of block 41 and the upper face of plate 43. Test fixture 40 is fixedly mounted on a lower plate 44 that is in turn fixedly mounted on the end of arm 21 remote from pulley 22. By appropriate mechanical or magnetic clamps (not shown), test fixture plate 43 is fixedly mounted on plate 44. Plate 43 has an upper surface which is prepared, by coating or suitable machining to represent one of the contacting surfaces to be tested for static coefficient or friction; the lower face of plate 42 as well as the upper and lower faces of block 41, is similarly prepared.

Figure 3:
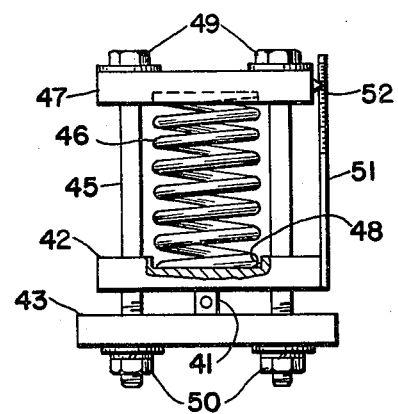
FIG. 3 is a side view of one embodiment of a test fixture that can be utilized with the apparatus of FIG. 2.

As illustrated in FIG. 3, extending upwardly from plate 43 are four threaded bolts 45 that form four columns for a keeper assembly for coil type, calibrated compression spring 46. The keeper assembly for compression spring 46 includes horizontally extending end plates 42 and 47 having bores through which bolts 45 freely extend. Each of plates 42 and 47 includes a centrally located, relatively shallow, cylindrical well 48 into which the ends of compression spring 46 are placed. Spring 46 is maintained in wells 48 by providing screw and washer assemblies 49 and 50 at the top and bottom of each of bolts 45, i.e., at the top and bottom faces of plates 47 and 43. Plate 44 is provided with recesses for receiving the downwardly depending bolt and washer assemblies 50.

Figure 4:
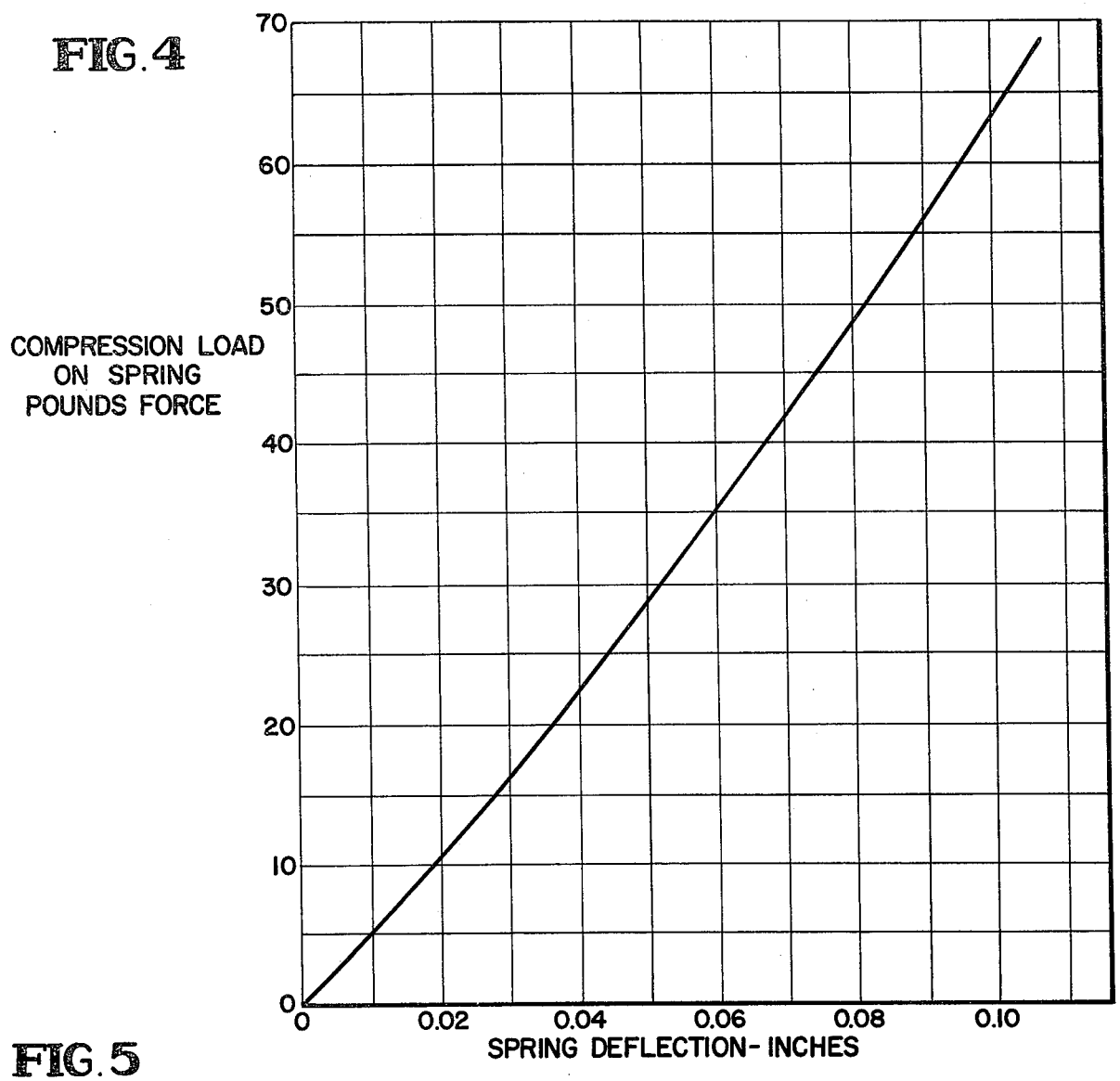
FIG. 4 is a calibration curve for a spring utilized in the test fixture of FIG. 3.

After test specimen 41 has been located between the upper and lower faces of plates 42 and 43 and one end of filament 32 has been connected to a tab (not shown) on the test specimen, the normal load between the tested surfaces of members 41, 42 and 43 is adjusted by varying the compression of spring 46. To this end, the top plate 47 is forced downward by tightening assemblies 49 to provide a desired deflection for the spring. To this end, spring 46 is calibrated as indicated in FIG. 4, which indicates the compressive load exerted by the spring on plate 42 as a function of spring deflection. By knowing the contacting surface area between test specimen 41 and plates 42 and 43, the stress on these members can be calculated as a function of deflection of spring 46. For example, if it is desired to provide a stress of 600 p.s.i., and the contact surface area between test specimen 41 and plate 42 is 1/16 square inch, achieved with a square test specimen having ¼ inch sides, which also equals the contact area between specimen 41 and plate 43, spring 46 exerts a load of 37.5 pounds on the upper surface of plate 42. To achieve a compressive spring load of 37.5 pounds, spring 46 is deflected 64 mils, as indicated by FIG. 4.

To enable the deflection of spring 46 to be easily ascertained, a vertically extending indicia member 51 is mounted on the top face of plate 42 and extends to pointer 52 that is carried on a vertically extending wall of plate 47. Thereby, in response to compression of spring 46, the indicia member and pointer 52 provide a ready indication of the spring deflection and of the load applied by the spring to the contact surfaces.

The apparatus of FIG. 2 functions similarly to that of FIG. 1, except that movement of test specimen 41 in response to the cyclic alternate tension and relaxation of filament 32 is relatively small. Also, because of the increased stress applied to the contacting surfaces being tested, each alternate tensioning and relaxation cycle is relatively long compared to the cycle for the apparatus of FIG. 1.

All of the parts forming the test fixture of FIG. 3 are fabricated of metal. Thereby, if it is desired to conduct a test for the static coefficient of friction in a vacuum environment, outgassing of materials from the metal surfaces into the vacuum is minimized and vacuum contamination does not occur after the initial outgassing operation has been performed.

While there have been described and illustrated several specific embodiments of the invention, it will be clear that variations in the details of the embodiments specifically illustrated and described may be made without departing from the true spirit and scope of the invention as defined in the appended claims. For example, while planar surfaces are specifically illustrated as being provided between test specimen 41 and plates 42 and 43, it is to be understood that the coefficient of friction for bodies having other than planar contacting surfaces can be determined by providing suitable seats on plates 42 and 43 to mate with the contact surfaces of the tested specimen.

What is claimed is:

1. A method of determining the static coefficient of friction between contacting surfaces of a plurality of bodies comprising the steps of applying a preselected constant load to the bodies normal to the contacting surfaces, fixedly connecting one portion of a flexible filament to a first of the bodies, another portion of the filament being fixedly connected to a stationary cross head, continuously moving a second of the bodies substantially vertically away from the stationary cross head at constant velocity while the one portion of the filament is connected through a guiding means to pull on the first body at right angles to the normal load so that the first body alternately is moved and then stopped relative to the second body across the contacting surfaces between the first and second bodies and the filament is alternately and cyclically tensioned and relaxed as the first body alternately is moved and then stopped, the maximum tension occurring at incipient stages of movement of the first body relative to the second body, measuring and recording the force applied to the first body at said maximum tensioning of the filament, and calculating the coefficient of friction in response to the measured forces and the force of the normal preselected constant load on the bodies with respect to time.

2. The method of claim 1 wherein the normal preselected constant load is applied to the contacting surfaces by applying a force normal to the contacting surfaces with a calibrated compression spring, deflecting the spring by a predetermined amount determined by a spring load versus deflection calibration response to provide a predetermined normal force on the contacting surfaces.

3. The method of claim 1 wherein the step of recording includes the step of displaying the measured force on an $x$–$y$ recorder that is deflected in one direction in response to the measured forces and is deflected in the other direction as the second body is being moved, and reading the maximum force indications from the recorder during the cyclic tensioning and relaxation of the filament.

4. A method of determining the static coefficient of friction between contacting surfaces of a plurality of bodies comprising the steps of applying a preselected constant load to the bodies normal to the contacting surfaces, while the preselected constant load is applied alternately and cyclically tensioning the relaxing a flexible filament that is fixedly connected to a first of the bodies and extends around a guiding means in a direction at right angles to the normal preselected constant load so that the first body alternately is moved and then stopped relative to a second of the bodies across the contacting surfaces between the first and second bodies while the second body moves parallel to the normal force, the maximum tensioning occurring at the incipient stages of movement of the first body relative to the second body, measuring and recording the force applied to the first body at said maximum tensioning of the filament, and calculating the coefficient of friction in response to the measured forces and the force of the normal preselected constant load on the bodies with respect to time.

5. A method of determining the static coefficient of friction between contacting surfaces of a plurality of bodies where the static coefficient of friction is appreciably greater than one, comprising the steps of applying a normal load on the contacting surfaces by fixedly connecting a first body of the bodies to a test fixture including a calibrated compression spring that exerts the normal force on the contacting surfaces, deflecting the spring by a predetermined amount determined by a spring load versus calibration response and the contact area between the contacting surfaces to provide a predetermined stress on the contacting surfaces, continuously moving the test fixture in a direction substantially parallel to the normal force while applying a force to a second body of the bodies in a direction at right angles to the normal force so that the second body alternately is moved and then stopped relative to the first body, measuring and recording the force required to cause each incipient movement of the second body relative to the first body in response to the applied force, and calculating the coefficient of friction in response to the measured force and the predetermined normal force with respect to time.

6. Apparatus for enabling the static coefficient of friction between contacting surfaces of a plurality of bodies to be determined comprising means for loading the bodies normal to the contacting surfaces, a flexible filament having a first portion adapted to be connected to a first body of the bodies and a second portion fixedly connected around a guiding means to a stationary cross head, means for continuously moving a second body of the bodies substantially vertically away from the stationary cross head at constant velocity so that the first body alternately is moved and then stopped relative to the second body across the contacting surfaces between them and the filament is alternately and cyclically tensioned and relaxed as the first body alternately is moved and then stopped, the maximum tension occurring at the incipient stages of movement of the first body relative to the second body, and means for measuring and recording with respect to time the force applied to the first body at the maximum tensioning of the filament during different cycles of filament tensioning and relaxing.

7. The apparatus of claim 6 wherein the recording means includes an $x$–$y$ recorder displaced in one direction in response to the measured force and displaced in a second direction as the second body is being moved substantially vertically away from the stationary cross head.

8. The apparatus of claim 6 wherein the means for loading comprises a test fixture into which the bodies are placed, said test fixture including a calibrated compression spring for applying the normal load to the contacting surfaces.

9. The apparatus of claim 8 further including means for varying the deflection of the compression spring to vary the normal load applied to the contacting surfaces.

10. The apparatus of claim 9 including indicia on the test fixture for indicating the spring deflection.

11. Apparatus for successively enabling data to be derived to determine the coefficient of static friction between contacting surfaces of a plurality of bodies comprising a fixed load cell, a flexible filament having one end secured to said load cell and extending vertically from the load cell, a horizontally extending and moveable cross arm positioned below the load cell, a low friction pulley fixedly mounted on the arm below the load cell, means for fixedly mounting a first body of the bodies on an upper surface of the cross arm, a second body of said bodies adapted to be connected to the other end of the filament, said filament extending vertically from the load cell over the pulley and horizontally to the second body, means for loading the bodies in the vertical direction, and motor means for continuously translating the cross arm substantially vertically away from the load cell at constant speed, whereby the second body alternately is moved and then stopped relative to the first body across a contacting surface between them and the filament is alternately and cyclically tensioned and relaxed as the second body alternately is moved and then stopped, the maximum tension occurring at the incipient stages of movement of the second body relative to the first body.

* * * * *